United States Patent
Privitera et al.

(10) Patent No.: US 8,349,449 B2
(45) Date of Patent: *Jan. 8, 2013

(54) POLYMER ACTIVE COMPLEX FIBERS

(75) Inventors: Marc Privitera, Walnut Creek, CA (US); David Jackson Lestage, Livermore, CA (US); Edward Jason White, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 479 days.

This patent is subject to a terminal disclaimer.

(21) Appl. No.: 12/120,898

(22) Filed: May 15, 2008

(65) Prior Publication Data

US 2009/0285718 A1    Nov. 19, 2009

(51) Int. Cl.
  *D02G 3/00* (2006.01)
(52) U.S. Cl. ...... 428/364; 428/372; 428/359; 428/375; 428/394; 524/464; 524/465; 977/762; 977/773; 977/788; 977/795
(58) Field of Classification Search .............. None
  See application file for complete search history.

(56) References Cited

U.S. PATENT DOCUMENTS

| | | | |
|---|---|---|---|
| 6,106,913 A | 8/2000 | Scardino et al. | |
| 6,554,881 B1 * | 4/2003 | Healey | 55/528 |
| 6,955,775 B2 * | 10/2005 | Chung et al. | 264/10 |
| 6,991,702 B2 | 1/2006 | Kim | |
| 7,229,944 B2 | 6/2007 | Shao-Horn et al. | |
| 7,335,629 B2 * | 2/2008 | Gentschev et al. | 510/311 |
| 7,569,359 B2 * | 8/2009 | McDonnell et al. | 435/31 |
| 2002/0100725 A1 | 8/2002 | Lee et al. | |
| 2002/0173213 A1 | 11/2002 | Chu et al. | |
| 2003/0215624 A1 | 11/2003 | Layman et al. | |
| 2005/0224998 A1 | 10/2005 | Andrady et al. | |
| 2006/0093820 A1 * | 5/2006 | Margarit-Puri et al. | 428/365 |
| 2006/0263417 A1 * | 11/2006 | Lelkes et al. | 424/443 |
| 2007/0009736 A1 * | 1/2007 | Chuang et al. | 428/364 |
| 2007/0237800 A1 * | 10/2007 | Lahann | 424/422 |
| 2007/0238635 A1 * | 10/2007 | Shah et al. | 510/447 |
| 2007/0272901 A1 * | 11/2007 | Gouma | 252/500 |
| 2009/0169630 A1 * | 7/2009 | Ward et al. | 424/489 |
| 2009/0202617 A1 * | 8/2009 | Ward et al. | 424/447 |
| 2009/0220378 A1 * | 9/2009 | McDonnell et al. | 422/55 |
| 2009/0285718 A1 * | 11/2009 | Privitera et al. | 422/30 |
| 2010/0080993 A1 * | 4/2010 | Privitera et al. | 428/401 |
| 2010/0112020 A1 * | 5/2010 | Westbroek et al. | 424/401 |
| 2010/0113857 A1 * | 5/2010 | Ramakrishna et al. | 588/299 |
| 2010/0215939 A1 * | 8/2010 | Westbroek et al. | 428/292.1 |
| 2010/0255581 A1 * | 10/2010 | Naqvi et al. | 435/396 |

FOREIGN PATENT DOCUMENTS

| | | |
|---|---|---|
| WO | WO 2004/074559 | 9/2004 |
| WO | WO 2005/004768 | 1/2005 |
| WO | WO 2005/005696 | 1/2005 |
| WO | WO 2005/005704 | 1/2005 |
| WO | WO 2007/002478 | 1/2007 |

OTHER PUBLICATIONS

"Electrospinning Process and Applications of Electrospun Fibers," Doshi and Remeker (J. Electrostatics, 35, 141 (1995).
"Beaded Nanofibers Formed During Electrospinning," Fong (Polymer, 40, 4584 (1999).

* cited by examiner

*Primary Examiner* — Jill Gray
(74) *Attorney, Agent, or Firm* — Erin Collins

(57) ABSTRACT

The invention covers a method of forming functionally active fibers and substrates including functionally active fibers. The method includes forming a mixture of at least one poly vinyl polymer and at least one bleaching active. The mixture is then injected at a controlled flow rate into an electric field to cause the mixture to at least partially form fine fibers that have an average diameter of less than about 1000 nanometers.

12 Claims, 1 Drawing Sheet

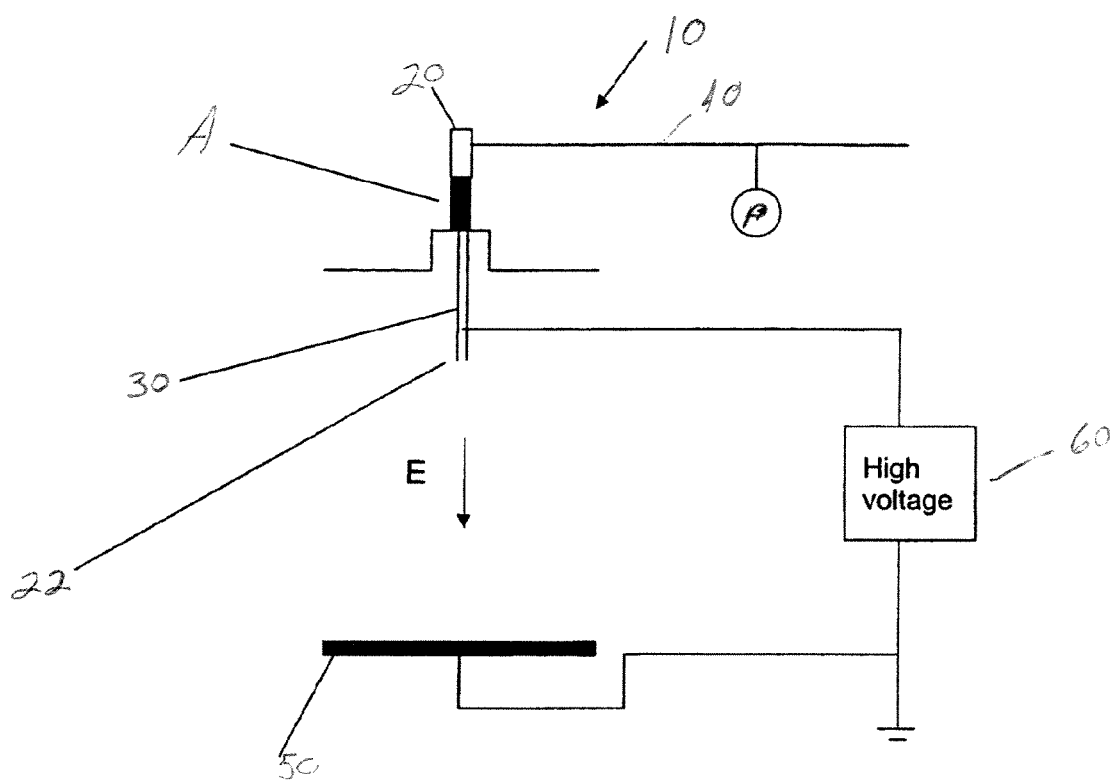
BACKGROUND ART

POLYMER ACTIVE COMPLEX FIBERS

The present invention is directed to electrospun fibers, and more particularly to electrospun fibers and a method of making the same which electrospun fibers include one or more functional actives

BACKGROUND OF THE INVENTION

The practice of electrospinning fibers from a polymer is still a relatively new practice. The electrospinning process has been used to form various types of polymers into fibers having a diameter of several nanometers. These small-diameter fibers have been found to have a large specific surface area relative to fibers, thus enabling the production of fibers having a high porosity.

Several processes for forming electrospun fibers, which can be used in the present invention, are disclosed in two articles entitled "Electrospinning Process and Applications of Electrospun Fibers" by Doshi and Reneker (J. Electrostatics, 35, 151 (1995)); and "Beaded nanofibers formed during electrospinning" by H. Fong (Polymer, 40, 4585 (1999)); PCT Application Serial Nos. WO 2004/074559; WO 2005/004768; WO 2005/005696; WO 2005/005704; WO 2007/002478; U.S. Pat. Nos. 6,106,913; 6,955,775; 6,991,702; 7,229,944; and U.S. Patent Publication Nos. 20020100725; 2002/0173213; 2003/0215624; 2005/0224998; all of which are incorporated by reference in their entirety.

The general process for forming a nanofiber includes pumping, extruding, etc. a polymer solution through one or more small openings and subjecting the polymer solution to an electric field to form nanofibers fibers that are collected on the surface of a collector. The process results in the conversion of a polymer solution into solid polymer fibers. The process can be used to control the fiber diameter (i.e., from several nanometers to several thousand nanometers), and to control the size of the pores in the fibers to produce a porous polymer fiber.

Due to the unique properties of electrospun fibers, it is believed that such electrospun fibers could be used for various types of cleaning applications. As such, it would be advantageous to use the porous polymer fiber to form a cleaning implement. It would also be advantageous to include one or more functional actives in the porous polymer fibers so as to enhance the cleaning, sanitizing and/or disinfecting properties of the porous polymer fibers. In view of the current state of the art regarding polymer electrospun fibers, there is a need for polymer electrospun fibers that include one or more functional actives, and which polymer electrospun fibers can be used in various types of cleaning scours and cleaning implements.

SUMMARY OF THE INVENTION

The present invention is directed to polymer electrospun fibers that include one or more functional actives. These electrospun fibers can be used in a variety of applications, all of which are included in the present invention. In one non-limiting application, the polymer electrospun fibers can be included in a variety of cleaning implements. Such cleaning implements can include, but are not limited to, sponges, brushes, foam pads, scouring pads, cleansing pads, dusters, wipes, mop heads, mop head wipes, rags, towels (e.g., paper, fabric, etc.), napkins (e.g., paper, fabric, etc.), tissues, toilet paper, etc. The polymer electrospun fibers can form the complete cleaning implement, or only form a part of the cleaning implement. When the polymer electrospun fibers only forms part of the cleaning implement, the polymer electrospun fibers can be bonded (e.g., adhesive, heat melted, lamination, etc.) to one or more other materials of the cleaning implement, interwoven with one or more other materials of the cleaning implement, needle punched to one or more other materials of the cleaning implement, mechanically connected to one or more other materials of the cleaning implement, or some combinations of such processes. As can be appreciated, other or additional arrangements can be used to incorporate the polymer electrospun fibers with one or more of the other materials of the cleaning implement. Although the polymer electrospun fibers are well suited for use in various types of cleaning implements and will be described with particular reference thereto, it will be appreciated that the polymer electrospun fibers can be used in other applications (e.g., gloves, clothing, masks, filters, carpet, upholstery, tablecloths, place mats, food and/or container mats, sheets, pillow cases, quilts, blankets, wash and bath towels, etc.).

In one non-limiting aspect of the present invention, the polymer electrospun fibers are formed from one or more polymers. In one non-limiting embodiment of the present invention, at least one of the polymers used in the polymer electrospun fibers is an at least partially water-soluble polymer, an at least partially alcohol-soluble polymer, an at least partially glycerol-soluble polymer, and/or at least glycol-soluble polymer. In one non-limiting aspect of this embodiment, all of the polymers used in the polymer electrospun fibers are at least partially water-soluble and/or alcohol soluble polymers. In another and/or alternative non-limiting aspect of this embodiment, all of the polymers used in the polymer electrospun fibers are at least partially water-soluble polymers. In yet another and/or alternative non-limiting aspect of this embodiment, all of the polymers used in the polymer electrospun fibers are water-soluble polymers. In still another and/or alternative non-limiting aspect of this embodiment, the polymer electrospun fibers are formed from a single polymer. In yet another and/or alternative non-limiting aspect of this embodiment, the polymer electrospun fibers are formed from two or more different polymers. In still yet another and/or alternative non-limiting aspect of this embodiment, all of the polymers used in the polymer electrospun fibers are alcohol-soluble polymers. The one or more polymers used in the polymer electrospun fibers can be a natural polymer and/or synthetic polymer. In another and/or alternative one non-limiting embodiment of the present invention, at least one of the polymers used in the polymer electrospun fibers is a synthetic polymer. In yet another and/or alternative one non-limiting embodiment of the present invention, at least one of the polymers used in the polymer electrospun fibers includes a poly vinyl polymer. In one non-limiting aspect of this embodiment, the poly vinyl polymer includes polymers of vinyl derivatives of pyrrolidone. Non-limiting examples of such vinyl derivatives of pyrrolidone include polyvinylpyrrolidone and poly(1-vinyl-2-pyrrolidone). As can be appreciated, other or additional polymers can be used in the present invention.

In another and/or alternative non-limiting aspect of the present invention, the one or more polymers used to form the polymer electrospun fibers are mixed with one or more functional actives prior to forming the polymer electrospun fibers so as to form electrospun fibers that facilitate in cleaning, sanitizing, disinfecting, and/or sterilizing a surface. As used herein, "functional active" refers to a substance, other than a surfactant, which reacts or interacts with a surface to clean, sanitize, disinfect, sterilize, bleach, remove stains, etc. such surface. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. At least a 99% reduction in bacterial population within a 24 hour time period is deemed "significant." As used herein, the term "sterilize" shall mean the substantially complete elimination or destruction of all forms of microbial life and which is authorized under the applicable regulatory laws to make legal claims as a "Sterilant" or to have sterilizing properties or qualities. Many different functional actives can be added to the one or more polymers. In one non-limiting embodiment of the invention, the polymer electrospun fibers of the present invention are formed from a single functional active. In another and/or alternative non-limiting embodiment of the invention, the polymer electrospun fibers of the present invention are formed from two or more different functional actives. In still another and/or alternative non-limiting embodiment of the invention, one or more of the functional actives that can be mixed with the one or more polymers include, but are not limited to, bleaching agents (e.g., peracids, perborates, percarbonates, chlorine-generating substances [e.g., chloroisocyanurates hypohalite sources], sodium hypochlorite, calcium hypochlorite, hydrogen peroxide, and/or sources of peroxides) and/or commercially formulated liquid cleaners that include one or more bleaching agents. As can be appreciated, other or additional functional actives can be used. In another and/or alternative non-limiting embodiment of the invention, many different types of commercial cleaners that include one or more bleaching agents can be used as the source of one or more functional actives. Non-limiting examples of commercial cleaners that can be used include, but are not limited to, several commercial products by The Clorox Company, namely Clorox® High Efficiency Bleach Cleaner, Clorox® Outdoor Bleach Cleaner, Clorox® Regular Bleach, Clorox® Scented Liquid Bleach, Clorox® Splash-Less Liquid Gel Bleach, and Clorox® Ultimate Care™ Premium Bleach. As can be appreciated, other or additional commercial products can be used. As can also be appreciated, two or more commercial cleaners can be mixed with one or more polymers to form the polymer electrospun fibers of the present invention. As can further be appreciated, one or more commercial cleaners can be combined with one or more functional actives from a non-commercial cleaner source and be mixed with one or more polymers to form the polymer electrospun fibers of the present invention. Also, it will be appreciated that the one or more functional actives which can be mixed with one or more polymers to form the polymer electrospun fibers of the present invention can be from a non-commercial cleaner source. In a further and/or alternative non-limiting embodiment of the invention, the polymer electrospun fibers can be formed from a mixture of one or more water-soluble bleaching agent compatible polymers and one or more bleaching actives (e.g, peracids, perborates, percarbonates, chlorine-generating substances [e.g., chloroisocyanurates hypohalite sources], sodium hypochlorite, calcium hypochlorite, hydrogen peroxide, and/or sources of peroxides, etc.).

In still another and/or alternative non-limiting aspect of the present invention, the one or more polymers and the one or more functional actives can be at least partially reacted or bonded together prior to forming the polymer electrospun fibers. In one non-limiting example, a vinyl derivative of pyrrolidone could be reacted with a peroxide or peroxide containing compound to form a peroxide derivative of the vinyl derivative of pyrrolidone. As can be appreciated, many other or additional derivatives can be formed for use in forming the polymer electrospun fibers. One non-limiting commercial available polymer that can be used in the present invention is Peroxydone® that is available from ISP. In this particular example, a single compound is used to form the mixture of polymer and functional active that is used in forming the polymer electrospun fibers. As such, as defined in the present invention, a single compound that includes a polymer and a functional active that is bonded to the polymer is considered a mixture of at least one polymer and at least one functional active when the single compound is at least partially dissolved in a solvent. As can be appreciated, additional polymers and/or functional actives could be mixed with a single compound that includes a polymer and functional active, wherein such mixture can be used in forming the polymer electrospun fibers; however, this is not required.

In yet another and/or alternative non-limiting aspect of the present invention, the one or more polymers and the one or more functional actives should be able to form a generally stable and homogeneous mixture. It has been found that when a generally stable and homogeneous mixture is not formed prior to the mixture being subjected to an electric field, few, if any, fibers are formed. As defined herein, a generally stable and homogeneous mixture is a polymer and functional active mixture that maintains its homogenous form for at least about 1 minute after being mixed for at least about 10 minutes. In one non-limiting embodiment of the invention, one or more polymers and one or more functional actives are selected such that a generally homogenous mixture is formed for at least about 5 minutes after being mixed for at least about 10 minutes. In another and/or alternative non-limiting embodiment of the invention, one or more polymers and one or more functional actives are selected such that a generally homogenous mixture is formed for at least about 15 minutes after being mixed for at least about 10 minutes. In still another and/or alternative non-limiting embodiment of the invention, one or more polymers and one or more functional actives are selected such that a generally homogenous mixture is formed for at least about 30 minutes after being mixed for at least about 10 minutes. In yet another and/or alternative non-limiting embodiment of the invention, one or more polymers and one or more functional actives are selected such that a generally homogenous mixture is formed for at least about 60 minutes after being mixed for at least about 10 minutes.

In still another and/or alternative non-limiting aspect of the present invention, at least one of the polymers used to form polymer electrospun fibers degrades or dissolves at a slower rate than at least one of the functional actives used to form the polymer electrospun fibers; however, this is not required. It is believed that an extended time of release of the one or more functional actives can be achieved during the use of the polymer electrospun fibers when at least one of the polymers used to form polymer electrospun fibers degrades or dissolves at a slower rate than at least one of the functional actives. As such, the usable life of the polymer electrospun fibers can be extended by this selection of polymer and functional active. In one non-limiting embodiment of the invention, all of the polymers in the polymer electrospun fibers degrade or dissolve at a slower rate than at least one of the functional actives in the polymer electrospun fibers. In another and/or alternative non-limiting embodiment of the invention, all of the polymers in the polymer electrospun fibers degrade or dissolve at a slower rate than all of the functional actives in the polymer electrospun fibers. In still another and/or alternative non-limiting embodiment of the invention, the time ratio that at least one of the polymers in the polymer electrospun fibers degrades or dissolves relative to at least one of the functional actives in the polymer electrospun fibers is at least about 1.05:1. As such, in this particular embodiment, if the functional active dissolved in 10 minutes, the polymer would dissolve in a time no earlier than 10.5 minutes. In yet another and/or alternative non-limiting embodiment of the invention, the time ratio that at least one of the polymers in the polymer electrospun fibers degrades or dissolves relative to at least one of the functional actives in the polymer electrospun fibers is at least about 1.25:1. In yet another and/or alternative non-limiting embodiment of the invention, the time ratio that at least one of the polymers in the polymer electrospun fibers degrades or dissolves relative to at least one of the functional actives in the polymer electrospun fibers is at least about 1.5:1. In still yet another and/or alternative non-limiting embodiment of the invention, the time ratio that at least one of the polymers in the polymer electrospun fibers degrades or dissolves relative to at least one of the functional actives in the polymer electrospun fibers is at least about 2:1. In another and/or alternative non-limiting embodiment of the invention, the time ratio that at least one of the polymers in the polymer electrospun fibers degrades or dissolves relative to at least one of the functional actives in the polymer electrospun fibers is about 2-10:1. As can be appreciated, other time ratios for dissolving rate of the functional active relative to the polymer can be used. In still another and/or alternative non-limiting embodiment of the invention, at least one of the polymers in the polymer electrospun fibers and at least one of the functional actives in the polymer electrospun fibers are designed to dissolve when exposed to water and/or alcohol. In one aspect of this embodiment, all of the polymers in the polymer electrospun fibers and all of the functional actives in the polymer electrospun fibers are designed to dissolve when exposed to water and/or alcohol.

In another and/or alternative non-limiting aspect of the present invention, when the polymer electrospun fibers are formed from one or more polymers that include a functional active bonded to the polymer, the functional active on the polymer is generally designed to disassociate from the polymer at a rate that is faster than the dissolving of the polymer when the electrospun fibers are exposed to water and/or an alcohol; however, this is not required. By selecting a polymer that dissolves at a slower rate than the rate at which the functional active disassociates from the polymer, the integrity of the electrospun fibers can be maintained while the functional active is controllably and/or uncontrollably released from the electrospun fibers. In one non-limiting embodiment of the invention, the time ratio that at least one of the polymers in the polymer electrospun fibers begins to dissolve relative to the time at least one of the functional actives disassociates from the polymer in the polymer electrospun fibers is at least about 2:1. As such, in this particular embodiment, if the functional active begins disassociating from the polymer in 5 seconds, the polymer would begin to dissolve in a time no earlier than 10 seconds. In another and/or alternative non-limiting embodiment of the invention, the time ratio that at least one of the polymers in the polymer electrospun fibers begins to dissolve relative to the time at least one of the functional actives disassociates from the polymer in the polymer electrospun fibers is at least about 5:1. In still another and/or alternative non-limiting embodiment of the invention, the time ratio that at least one of the polymers in the polymer electrospun fibers begins to dissolve relative to the time at least one of the functional actives disassociates from the polymer in the polymer electrospun fibers is at least about 20:1. In yet another and/or alternative non-limiting embodiment of the invention, the time ratio that at least one of the polymers in the polymer electrospun fibers begins to dissolve relative to the time at least one of the functional actives disassociates from the polymer in the polymer electrospun fibers is at least about 100:1. As can be appreciated, other time ratios for at least one of the polymers in the polymer electrospun fibers to begin dissolving relative to the time at least one of the functional actives disassociates from the polymer in the polymer electrospun fibers can be used.

In another and/or alternative non-limiting aspect of the present invention, the viscosity of the mixture of the at least one polymer and the at least one functional active prior to the mixture being subjected to an electric field is at least about 500 cps at 25° C. It has been found that viscosities that are lower than about 500 cps at 25° C. will not properly form polymer electrospun fibers, or not form any polymer electrospun fibers. The viscosity of the mixture of the at least one polymer and the at least one functional active prior to the mixture being subjected to an electric field is also less than about 100000 cps at 25° C. It has been found that viscosities that are greater than about 100000 cps at 25° C. also will not properly form polymer electrospun fibers, or not form any polymer electrospun fibers. In one non-limiting embodiment of the invention, the viscosity of the mixture of the at least one polymer and the at least one functional active prior to the mixture being subjected to an electric field is at least about 750 cps at 25° C. In another and/or alternative non-limiting embodiment of the invention, the viscosity of the mixture of the at least one polymer and the at least one functional active prior to the mixture being subjected to an electric field is at least about 1000 cps at 25° C. In still another and/or alternative non-limiting embodiment of the invention, the viscosity of the mixture of the at least one polymer and the at least one functional active prior to the mixture being subjected to an electric field is no greater than about 25000 cps at 25° C. In still another and/or alternative non-limiting embodiment of the invention, the viscosity of the mixture of the at least one polymer and the at least one functional active prior to the mixture being subjected to an electric field is no greater than about 10000 cps at 25° C. In yet another and/or alternative non-limiting embodiment of the invention, the viscosity of the mixture of the at least one polymer and the at least one functional active prior to the mixture being subjected to an electric field is about 1500-8000 cps at 25° C. In still yet another and/or alternative non-limiting embodiment of the invention, the viscosity of the mixture of the at least one polymer and the at least one functional active prior to the mixture being subjected to an electric field is about 2000-7000 cps at 25° C. As can be appreciated, other viscosities for the mixture can be used.

In still another and/or alternative non-limiting aspect of the present invention, the process parameters regarding flow rate of the polymer-functional additive mixture, strength of electric field and distance mixture travels through electric field are controlled to obtain the polymer electrospun fibers. It has been found that by controlling these parameters, a desired thin fiber-structured polymer material can be formed in accordance with the present invention. In one non-limiting embodiment of the invention, the flow rate of the mixture the polymer-functional additive mixture through each nozzle is at least about 0.1 microliter per minute and less than about 100 microliters per minute. It has been found that faster or slower flow rates for the mixture through each nozzle will produce little, if any, polymer electrospun fibers. In one non-limiting aspect of this embodiment, the flow rate of the mixture the polymer-functional additive mixture through each nozzle is at least about 5 microliters per minute. In another and/or alternative non-limiting aspect of this embodiment, the flow rate of the mixture the polymer-functional additive mixture through each nozzle is at least about 7 microliters per minute. In still another and/or alternative non-limiting aspect of this embodiment, the flow rate of the mixture the polymer-functional additive mixture through each nozzle is at least about 10 microliters per minute. In yet another and/or alternative non-limiting aspect of this embodiment, the flow rate of the mixture the polymer-functional additive mixture through each nozzle is no greater that about 60 microliters per minute. In still yet another and/or alternative non-limiting aspect of this embodiment, the flow rate of the mixture the polymer-functional additive mixture through each nozzle is no greater that about 40 microliters per minute. In another and/or alternative non-limiting aspect of this embodiment, the flow rate of the mixture the polymer-functional additive mixture through each nozzle is no greater that about 30 microliters per minute. As can be appreciated, other or additional flow rates for the mixture can be used. In another and/or alternative non-limiting embodiment of the invention, the strength of the electric field through which the mixture travels as the mixture is transformed into polymer electrospun fibers is at least about 0.5 kV and less than about 200 kV. It has been found that an electric field that is less than 0.5 kV will not form polymer electrospun fibers. Likewise, it has been found that an electric field that is 200 kV or more also will not form polymer electrospun fibers. In one non-limiting aspect of this embodiment, the electric field through which the mixture travels as the mixture is transformed into polymer electrospun fibers is at least about 1 kV. In another and/or alternative non-limiting aspect of this embodiment, the electric field through which the mixture travels as the mixture is transformed into polymer electrospun fibers is at least about 2 kV. In still another and/or alternative non-limiting aspect of this embodiment, the electric field through which the mixture travels as the mixture is transformed into polymer electrospun fibers is up to about 100 kV. In yet another and/or alternative non-limiting aspect of this embodiment, the electric field through which the mixture travels as the mixture is transformed into polymer electrospun fibers is about 2-20 kV. In still yet another and/or alternative non-limiting aspect of this embodiment, the electric field through which the mixture travels as the mixture is transformed into polymer electrospun fibers is about 2-12 kV. In another and/or alternative non-limiting aspect of this embodiment, the electric field through which the mixture travels as the mixture is transformed into polymer electrospun fibers is about 2-10 kV. As can be appreciated, other or additional values for the electric field can be used. In still another and/or alternative non-limiting embodiment of the invention, the distance that the mixture of polymer and functional active travels through the electric field during the transformation from a liquid mixture to polymer electrospun fibers is at least about 1 cm and typically less than about 100 cm. It has been found that distances of travel of less than 1 cm are insufficient to form polymer electrospun fibers. Distances of travel of greater than 100 cm are not required since the polymer electrospun fibers have been fully created long before traveling of such distances. In one non-limiting aspect of this embodiment, the distance that the mixture of polymer and functional active travels through the electric field during the transformation from a liquid mixture to polymer electrospun fibers is at least about 2 cm. In another non-limiting aspect of this embodiment, the distance that the mixture of polymer and functional active travels through the electric field during the transformation from a liquid mixture to polymer electrospun fibers is up to about 40 cm. In still another non-limiting aspect of this embodiment, the distance that the mixture of polymer and functional active travels through the electric field during the transformation from a liquid mixture to polymer electrospun fibers is up to about 20 cm. In yet another non-limiting aspect of this embodiment, the distance that the mixture of polymer and functional active travels through the electric field during the transformation from a liquid mixture to polymer electrospun fibers is about 2-10 cm. As can be appreciated, other or additional distances of travel can be used.

In yet another and/or alternative non-limiting aspect of the present invention, the polymer electrospun fibers are nanofibers. As defined herein, a nanofiber is a fiber that has an average diameter of no more than 1000 nanometers. In one non-limiting embodiment of the invention, the polymer electrospun fibers have an average diameter of no more than about 500 nanometers. In another and/or alternative non-limiting embodiment of the invention, the polymer electrospun fibers have an average diameter of no more than about 200 nanometers. In still another and/or alternative non-limiting embodiment of the invention, the polymer electrospun fibers have an average diameter of no more than about 100 nanometers. In yet another and/or alternative non-limiting embodiment of the invention, the polymer electrospun fibers have an average diameter of at least about 0.1 nanometers. In still yet another and/or alternative non-limiting embodiment of the invention, the polymer electrospun fibers have an average diameter of at least about 0.5 nanometers. In another and/or alternative non-limiting embodiment of the invention, the polymer electrospun fibers have an average diameter of at least about 1 nanometers.

In still yet another and/or alternative non-limiting aspect of the present invention, the polymer electrospun fibers can include one or more additives; however, this is not required. Such one or more additives, when used, can include, but are not limited to, abrasive materials, anti-corrosion materials, anti-redeposition materials, anti-static agents, anti-sticking agents, buffering and pH adjusting agents, chelating agents, colorants and/or dyes, defoamers, elastomers, enzymes, filler materials, foamers, fragrances or perfumes, heat generating materials, hydrotropes, sequestration agents, softening agents, soil release agents, solubilizing materials, stabilizers, surfactants, sudsing control agents, thickeners, wetting agents, and/or UV protectors. As can be appreciated, other or additional additives can be used.

It is one non-limiting object of the present invention to form polymer electrospun fibers from a mixture that includes at least one polymer and at least one bleaching active.

It is another and/or alternative object of the present invention to form polymer electrospun fibers from a modified polymer that includes at least one bleaching agent.

It is still another and/or alternative object of the present invention to form polymer electrospun fibers from at least one water-soluble and/or alcohol soluble polymer that includes at least one bleaching agent.

It is still yet another and/or alternative object of the present invention to form polymer electrospun fibers having a high surface area to weight ratio.

These and other objects and advantages will become apparent to those skilled in the art upon reading and following the description of the invention taken together with the accompanied drawings.

BRIEF DESCRIPTION OF THE DRAWING

Reference may now be made to the drawings, which illustrates various attributes of the invention wherein;

a. FIG. 1 is a schematic illustration of a conventional electrospinning arrangement.

DETAILED DESCRIPTION OF THE PREFERRED EMBODIMENT

Referring now to the drawings wherein the showings are for the purpose of illustrating preferred embodiments of the invention only and not for the purpose of limiting same, FIG. 1 illustrates a schematic illustration of a conventional electrospray/electrospinning apparatus 10 for producing fibers and/or fibrous materials. As used herein, the term fibrous materials denotes material both electrosprayed as short fibers and material electrospun into longer continuous fibers. In accordance with one non-limiting embodiment of the present invention, a spray head 20 includes an electrode 30 that is connected to the spray head. The spray head 20 includes at least one spray nozzle 22. Generally, nozzle 22 is a spinning nozzle. The spray head is connected to a pipe or tube 40 in communication with a supply of electrospray medium A. The electrospray medium is an extrudable mixture that includes at least one polymer and at least one functional active.

An electric potential across to the electrodes 30 and 50 that is generated by a high voltage source 60 creates an electric field E which extends through and beyond nozzle 22 of the spray head 20 to the exterior electrode 50. The geometrical arrangement of the electrode 30 and the exterior electrode 50 configures the electric field strength and distribution. The electrospray medium, upon extrusion from the spray head, is guided along a direction of the electric field E toward the exterior electrode 50. Electrode 50 is generally connected to a plate or moving conveyor that is used to collect the formed electrospun fibers.

The flowrate at which the electrospray medium flows through the nozzle of the spray head can be at least partially controlled by the size of the nozzle and the pressure generated exerted on the electrospray medium by pump P. One non-limiting pump that can be used is a NE-1000 programmable syringe pump. As can be appreciated, many arrangements for forming the electrospun fibers can be used. The electrospray medium is formulated to form fibers that have a large surface area to weight ratio. The fibers of the present invention generally have an average diameter of less than about 1000 nanometers. These types of fibers can be useful in various types of cleaning applications. For example, the cleaning efficacy of various types of cleaning implements (e.g., wipes, sponges, towels, mops, brushes, etc.) can be improved by incorporating the fibers of the present invention into such cleaning implements, without having to increase the volume of functional actives in the cleaning implement. The large surface area of the fibers of the present invention can be used to inhibit excess amount of cleaning agents from becoming diluted and/or flushed from the cleaning implement by water, at the point that the cleaning implement contacts a surface to be cleaned. The fibers of the present invention can be incorporated into non-woven cleaning implements (e.g. sponges, foam pads, wipes, etc.), laminated and/or adhesively connected to various types of cleaning implements, etc. The fibers of the present invention can be used to deliver low-levels of a functional active in a controlled or uncontrolled release profile. The fibers of the present invention can be used to stabilize and/or strengthen a functional active that is incorporated in the fiber. As such, the fibers can be used to deliver functional active to a desired surface which was in the past a normally difficult functional active to deliver at a point of use.

A non-limiting example for forming fibers of the present invention will now be set forth. The fibers in this non-limiting example were formed from a mixture of a water soluble polymer that has been modified to include a bleaching agent.

A solution of polyvinylpyrrolidone is reacted with a peroxide compound to incorporate peroxide compound as a functional group on the polyvinylpyrrolidone. The peroxide bonded complex of polyvinylpyrrolidone is a water-soluble polymer. The peroxide bonded complex of polyvinylpyrrolidone is dissolved in water to form the electrospray medium. The viscosity of the solution as maintained between 2000-7000 cps at 25° C. The electrospray medium is a stable and homogenous phase so that the mixture could be electrospun.

The polyvinylpyrrolidone polymer used in the electrospray medium dissolves more slowly than the time period it takes the peroxide group to disassociate from the polyvinylpyrrolidone.

The solution was slowly pumped through a spinning nozzle at a volume of about 5-30 microliters/minute. The solution exiting the spinning nozzle was exposed to an electric field of about 10-20 kV. The solution traveled a distance of about 5-20 cm from the spinning nozzle to a collector which collected the formed fibers. The average diameter of the formed fibers was about 100-500 nanometers. The formed fibers produced a porous web of a high porosity.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. An electrospun functionally active nanofiber comprising: a homogenous mixture of one or more polymer and one or more bleaching agent, wherein said polymer and said bleaching agent are at least partially reacted or bonded together, said polymer is at least partially water-soluble, at least partially ethanol-soluble, at least partially glycerol-soluble, or combinations thereof, said bleaching agent is selected from the group consisting of peracids, perborates, percarbonates, sodium hypochlorite, calcium hypochlorite, peroxides, or mixtures thereof, optionally, said mixture includes one or more additives, anti-corrosion materials, anti-redeposition materials, anti-static agents, anti-sticking agents, buffering and pH adjusting agents, chelating agents, defoamers, elastomers, enzymes, filler materials, foamers, fragrances or perfumes, heat generating materials, hydrotropes, sequestration agents, softening agents, soil release agents, solubilizing materials, stabilizers, surfactants, sudsing control agents, thickeners, solvents, wetting agents, and-UV protectors, said mixture having a viscosity of said mixture about 1000-10000 cps at 20° C., said mixture of one or more polymer, one or more bleaching agent and one or more additives, together forms a homogenous composition that is formed into a homogenous nanofiber that has an average diameter of less than about 1000 nanometers, said polymer designed to dissolve in water at a slower rate than said bleaching agent so as to extend the time of release of said bleaching agent from said polymer and thereby extend cleaning time and efficacy of said electrospun functionally active nanofiber.

2. The electrospun functionally active nanofiber as defined in claim 1, wherein said polymer is a poly vinyl polymer.

3. The electrospun functionally active nanofiber as defined in claim 2, wherein said poly vinyl polymer includes polymers of vinyl derivatives of pyrrolidone.

4. The electrospun functionally active nanofiber as defined in claim 1, wherein said nanofiber is designed to deliver a controlled release of a functional active comprising at least one bleaching agent.

5. The electrospun functionally active nanofiber as defined in claim 1, wherein said average diameter of said fibers is about 25-200 nanometers.

6. The electrospun functionally active nanofiber as defined in claim 1, wherein said polymer and said bleaching agent are homogeneously mixed in a solvent, wherein said solvent comprises one or more of the following components: water, an alcohol, or mixtures thereof, until said polymer and at least one bleaching agent are completely soluble in said solvent prior to said forming said nanofiber, said formed nanofiber has homogenous composition.

7. An electrospun functionally active nanofiber as defined in claim 1 comprising: a water-soluble polymer that has been modified to include a bleaching agent that is then dissolved in water to form an electrospray medium that is a stable and homogenous mixture comprising: said polymer, said bleaching agent, water and one or more additives, and wherein said electrospray medium is electropsun into functionally active nanofibers having a homogenous composition.

8. An electrospun functionally active nanofiber according to claim 7, wherein the water-soluble polymer a poly vinyl polymer.

9. An electrospun functionally active nanofiber according to claim 7, wherein the bleaching agent comprises peroxide.

10. An electrospun functionally active nanofiber according to claim 7, wherein said additive is selected from the group consisting of: anti-corrosion materials, anti-redeposition materials, anti-static agents, anti-sticking agents, buffering and pH adjusting agents, chelating agents, defoamers, elastomers, enzymes, filler materials, foamers, fragrances or perfumes, heat generating materials, hydrotropes, sequestration agents, softening agents, soil release agents, solubilizing materials, stabilizers, surfactants, sudsing control agents, thickeners, wetting agents, and UV protectors.

11. An electrospun functionally active nanofiber according to claim 7, wherein the nanofiber is substantially free of: a chemical indicator, a physical indicator or a biological indicator.

12. An electrospun functionally active nanofiber according to claim 7, wherein the nanofiber is substantially free of encapsulated actives.

\* \* \* \* \*